United States Patent
Kothari et al.

(10) Patent No.: US 8,394,128 B2
(45) Date of Patent: Mar. 12, 2013

(54) MODULATED CONSTRAINING APPARATUS AND METHODS OF USE

(75) Inventors: Manish Kothari, San Rafael, CA (US);
Louis Fielding, San Carlos, CA (US);
Colin Cahill, Portola Valley, CA (US);
Anand Parikh, San Diego, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 0 days.

(21) Appl. No.: 13/095,586

(22) Filed: Apr. 27, 2011

(65) Prior Publication Data
US 2012/0109199 A1    May 3, 2012

Related U.S. Application Data

(63) Continuation of application No. PCT/US2009/064217, filed on Nov. 12, 2009.

(60) Provisional application No. 61/113,718, filed on Nov. 12, 2008.

(51) Int. Cl.
*A61B 17/88* (2006.01)

(52) U.S. Cl. ............ 606/279; 606/74; 606/77; 606/105; 606/246; 606/248; 606/908

(58) Field of Classification Search .................... 606/74, 606/103, 105, 247, 248, 249, 322
See application file for complete search history.

(56) References Cited

U.S. PATENT DOCUMENTS

| | | | |
|---|---|---|---|
| 2,987,062 A | 6/1961 | Ellison | |
| 5,092,866 A | 3/1992 | Breard et al. | |
| 5,993,452 A | 11/1999 | Vandewalle | |
| 6,402,750 B1 | 6/2002 | Atkinson et al. | |
| 6,582,433 B2 * | 6/2003 | Yun | 606/249 |
| 6,828,357 B1 | 12/2004 | Martin et al. | |
| 7,201,751 B2 | 4/2007 | Zucherman et al. | |
| 7,291,150 B2 | 11/2007 | Graf | |
| 7,377,921 B2 | 5/2008 | Studer et al. | |
| 2002/0095154 A1 * | 7/2002 | Atkinson et al. | 606/61 |
| 2002/0147449 A1 * | 10/2002 | Yun | 606/61 |
| 2002/0151978 A1 | 10/2002 | Zacouto et al. | |
| 2003/0040746 A1 * | 2/2003 | Mitchell et al. | 606/61 |
| 2003/0135267 A1 * | 7/2003 | Solem et al. | 623/1.18 |
| 2004/0215341 A1 | 10/2004 | Sybert et al. | |
| 2005/0192581 A1 | 9/2005 | Molz et al. | |
| 2005/0203624 A1 | 9/2005 | Serhan et al. | |
| 2005/0216017 A1 * | 9/2005 | Fielding et al. | 606/74 |

(Continued)

FOREIGN PATENT DOCUMENTS

| | | |
|---|---|---|
| CN | 201101572 Y | 8/2008 |
| FR | 2774581 A1 | 8/1999 |

OTHER PUBLICATIONS

European search report and opinion dated Mar. 15, 2012 for EP Application No. 9856756.0.

(Continued)

*Primary Examiner* — Eduardo C Robert
*Assistant Examiner* — Jerry Cumberledge
(74) *Attorney, Agent, or Firm* — Wilson Sonsini Goodrich & Rosati

(57) ABSTRACT

A constraining apparatus includes a constraining structure that captures a first and a second anatomical structure. A motion limiting member coupled with the constraining structure is adapted to provide a force resistant to relative movement of the first anatomical structure away from the second anatomical structure. A regulating member is detachably coupled with the motion limiting member or the constraining structure and is adapted to change the resistant force provided by the motion limiting member when the regulating member is in direct engagement with the motion limiting member or constraining structure.

17 Claims, 10 Drawing Sheets

U.S. PATENT DOCUMENTS

| | | |
|---|---|---|
| 2005/0267470 A1 | 12/2005 | McBride |
| 2006/0036240 A1 | 2/2006 | Colleran et al. |
| 2006/0184230 A1* | 8/2006 | Solem et al. .................. 623/1.15 |
| 2006/0214069 A1* | 9/2006 | Schiebler ..................... 248/74.3 |
| 2006/0247623 A1* | 11/2006 | Anderson et al. ............... 606/61 |
| 2006/0293662 A1 | 12/2006 | Boyer, II et al. |
| 2007/0043360 A1* | 2/2007 | Thramann ....................... 606/61 |
| 2007/0173818 A1 | 7/2007 | Hestad et al. |
| 2007/0270814 A1 | 11/2007 | Lim et al. |
| 2007/0270855 A1 | 11/2007 | Partin |
| 2007/0276369 A1 | 11/2007 | Allard |
| 2007/0276380 A1 | 11/2007 | Jahng et al. |
| 2008/0051784 A1 | 2/2008 | Gollogly et al. |
| 2008/0086199 A1* | 4/2008 | Dave et al. ................... 623/1.42 |
| 2008/0103601 A1 | 5/2008 | Biro et al. |
| 2008/0108993 A1 | 5/2008 | Bennett et al. |
| 2008/0177264 A1 | 7/2008 | Alamin et al. |
| 2008/0183209 A1 | 7/2008 | Robinson et al. |
| 2008/0262549 A1 | 10/2008 | Bennett et al. |
| 2009/0264927 A1* | 10/2009 | Ginsberg et al. .............. 606/246 |

OTHER PUBLICATIONS

International search report and written opinion dated Jan. 20, 2010 for PCT/US2009/064217.

* cited by examiner

MODULATED CONSTRAINING APPARATUS AND METHODS OF USE

CROSS-REFERENCE TO RELATED APPLICATIONS

This application is a continuation of International Patent Application No. PCT/US2009/064217 filed Nov. 12, 2009, which claims the benefit of 61/113,718 filed Nov. 12, 2008, the contents of which are incorporated herein by reference.

BACKGROUND OF THE INVENTION

1. Field of the Invention

The present invention generally relates to medical methods and devices. More particularly, the present invention relates to methods and regulated or modulated constraining devices used for holding structures together. These constraint devices may be used to hold anatomical structures such as bones together with higher holding forces at the beginning of the healing process when more support is needed and lower holding forces later on as healing progresses and less support is desired. Other embodiments work in an opposite manner and provide increased holding forces over time. By varying the holding forces over time, a single device may be used to accommodate different phases of the healing process and automatically adjust the length or tension in the constraining device without requiring additional surgery. Exemplary internal fixation procedures include repair of fractured bones and cerclage of a spinal segment in patients with segmental back pain or segmental instability such as in degenerative spondylolisthesis.

Current repair of fractured bones may involve the use of an internal fixation device. For example, an exemplary use of an internal fixation device is to facilitate repair of a fractured greater trochanter. In current procedures, a stiff cable may be wrapped around the fractured portions of bone in order to hold them together during healing. The cable typically provides relatively constant holding forces over the course of the healing process. This is not always desirable. In some cases, it is desirable to firmly hold the fractured bones together at the beginning of the healing process. However, over time as the bone heals, a constant fixation force can stress shield the tissue which can hamper healing later on as the tissue remodels to accommodate a lower load. Higher compressive forces may also cause bone necrosis. Additionally, it may be desirable to allow a small amount of micromotion or a small amount of loading in order to promote tissue repair. Thus it would be advantageous to provide a device that can vary the holding forces as the healing process advances. In other cases, it might be advantageous to provide a device that increases the holding force over time. This allows slack or loosening that may develop over time to be taken up as healing progresses.

Internal fixation is also used to treat patients with low back pain resulting from internal disc disruption or discogenic disease. This includes the use of bone cerclage devices. There are a number of different types of cerclage devices. One type uses an inelastic cable to encircle the spinous processes or other vertebral elements thereby restraining motion. Another type of cerclage involves the use of an elastic tether structure coupled to the spinal segment. Some cerclage devices include the use of a spacer implanted between adjacent spinous processes. While these approaches are promising, they all have potential shortcomings. For example, some of these devices are invasive and require removal of surrounding ligaments, and others are designed for static applications and thus limit motion of the affected spinal segment. This may be advantageous at the beginning of healing when immobilization helps improve the likelihood of concomitant fusion but is undesirable later on in the healing process when some motion is desirable. Still other devices allow substantially unrestricted spinal extension but the constraining force provided by the device is either pre-set or related to the extent of spinal segment motion and therefore the devices do not vary the fixation forces during the course of the healing process.

Discogenic disease is also associated with degenerative spondylolisthesis, a spinal condition in which abnormal segmental translation is exacerbated by segmental flexion. Treatment for degenerative spondylolisthesis often involves removal of bone or other tissue causing the nerve impingement (decompression surgery), combined with bone fusion to prevent further instability. Since bone fusion takes time, often the entire segment is also immobilized or stabilized (sometimes referred to as fused) using instrumentation, for example, pedicle screws and stabilization rods. This relatively rigid instrumentation often offloads the implanted fusion material, which needs some loading for strong bone formation. Moreover, the instrumentation remains rigid over time. Therefore, again it would be useful to provide a fixation device that can vary the holding or fixation forces over the course of the healing process.

While the constraint devices discussed above are promising, they often provide consistent fixation until they are removed, if at all. Thus the constraint devices shield the healing tissue from stress. This is often desirable at the early phase of healing, but can hamper tissue repair as the tissue remodels. Additionally, in some cases, it is also desirable to permit a small amount of motion or a small amount of loading, as this facilitates tissue repair. Furthermore, it may be desirable initially to protect the healing tissue from high impact loading through the use of a damping mechanism. Therefore, for the aforementioned reasons there is a need to provide a constraint device which can vary the properties of the device, such as holding force, during the healing or tissue regeneration process. In particular, such a device should be minimally invasive and easily adjustable by a physician during the healing process. It would also be desirable for such a device to automatically vary the device's constraining properties over time. Additionally, the device's constraining properties could vary based on sensing the evolving mechanical or biochemical environment or based on an induced change to the device environment.

2. Description of the Background Art

Patents and published applications of interest include: U.S. Pat. Nos. 3,648,691; 4,643,178; 4,743,260; 4,966,600; 5,011,494; 5,092,866; 5,116,340; 5,180,393; 5,282,863; 5,395,374; 5,415,658; 5,415,661; 5,449,361; 5,456,722; 5,462,542; 5,496,318; 5,540,698; 5,562,737; 5,609,634; 5,628,756; 5,645,599; 5,725,582; 5,902,305; Re. 36,221; 5,928,232; 5,935,133; 5,964,769; 5,989,256; 6,053,921; 6,248,106; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; 7,029,475; 7,163,558; Published U.S. Patent Application Nos. US 2002/0151978; US 2004/0024458; US 2004/0106995; US 2004/0116927; US 2004/0117017; US 2004/0127989; US 2004/0172132; US 2004/0243239; US 2005/0033435; US 2005/0049708; 2005/0192581; 2005/0216017; US 2006/0069447; US 2006/0136060; US 2006/0240533; US 2007/0213829; US 2007/0233096; 2008/0009866; 2008/0108993; Published PCT Application Nos. WO 01/28442 A1; WO 02/03882 A2; WO 02/051326 A1; WO 02/071960 A1; WO 03/045262 A1;

WO2004/052246 A1; WO 2004/073532 A1; WO2008/051806; WO2008/051423; WO2008/051801; WO2008/051802; and Published Foreign Application Nos. EP0322334 A1; and FR 2 681 525 A1. The mechanical properties of flexible constraints applied to spinal segments are described in Papp et al. (1997) Spine 22:151-155; Dickman et al. (1997) Spine 22:596-604; and Garner et al. (2002) Eur. Spine J. S186-S191; Al Baz et al. (1995) Spine 20, No. 11, 1241-1244; Heller, (1997) Arch. Orthopedic and Trauma Surgery, 117, No. 1-2:96-99; Leahy et al. (2000) Proc. Inst. Mech. Eng. Part H: J. Eng. Med. 214, No. 5: 489-495; Minns et al., (1997) Spine 22 No. 16:1819-1825; Miyasaka et al. (2000) Spine 25, No. 6: 732-737; Shepherd et al. (2000) Spine 25, No. 3: 319-323; Shepherd (2001) Medical Eng. Phys. 23, No. 2: 135-141; and Voydeville et al (1992) Orthop Traumatol 2:259-264.

BRIEF SUMMARY OF THE INVENTION

The present invention relates to methods and apparatus used to constrain anatomical structures. More specifically, the present invention relates to apparatus and methods for regulating the forces provided by the constraint device. Exemplary use of such a regulated constraint device includes orthopedic internal fixation procedures such as treatment of patients having spinal pain or fractured bones.

In a first aspect of the present invention, a constraining apparatus comprises a constraining structure adapted to capture a first and a second anatomical structure. A motion limiting member is coupled with the constraining apparatus and provides a force resistant to relative movement of the first anatomical structure away from the second anatomical structure. A regulating member is coupled with the motion limiting member or the constraining structure and is adapted to change the resistant force provided by the motion limiting member when the regulating member in direct engagement with the motion limiting member or the constraining structure.

The first anatomical structure may comprise a first spinous process and the second anatomical structure may comprise a second spinous process or sacrum. Sometimes, a third spinous process may be disposed between the first spinous process and the second spinous process or sacrum. The first anatomical structure may comprise a bone such as a greater trochanter and the second anatomical structure may comprise a portion of the bone fractured or cut therefrom.

The constraining structure may comprise a substantially inelastic tether such as a strap. The motion limiting member may comprise a compliance member such as a spring and may also be integral with the constraining structure. The motion limiting member may also comprise a damper element. Sometimes the compliance member may comprise an elastomer. Some embodiments of the apparatus may further comprise a second compliance member that is coupled with the constraining structure.

The regulating member may be detachably coupled with the motion limiting member. The regulating member may comprise a pin joint that pivotably couples the compliance member and the constraining structure so as to allow realignment of the constraining apparatus in response to expansion or contraction of adjacent tissue. The regulating member may comprise a bioabsorbable cover or block encasing or embedding at least a portion of the motion limiting member thereby limiting movement of the motion limiting member and also increasing its stiffness. The bioabsorbable cover may also encase a portion of the motion limiting member in a deformed configuration such that upon erosion of the cover the regulating member is biased to return to its undeformed configuration thereby regulating the tightness of the constraining device. The deformed configuration may be an expanded state whereby returning to the undeformed configuration tightens the constraint; or conversely the deformed configuration may be a compressed or contracted state, whereby returning to the undeformed configuration loosens the constraint. The cover may be polylactic acid or polyglycolic acid, for example. The regulating member may comprise a locking mechanism for locking the regulating member in either an expanded or contracted configuration, and may also comprise a damper element that absorbs transient loads or motions. The damper may comprise a viscoelastic material or the damper may absorb transient loads or motions due to friction between components in the damper. The damper may comprise a biodegradable component which biodegrades away resulting in an adjustment to the damping effect. The damper may be in parallel with the motion limiting member or in series. The apparatus may further comprise a second damper element that is coupled with the tether structure.

In other embodiments, the regulating member may comprise a restraint that is detachably coupled with the motion limiting member. The restraint may comprise a clip, wherein engagement of the clip with the motion limiting member increases the motion limiting member stiffness and disengagement of the clip from the motion limiting member decreases its stiffness. The restraint may be bioabsorbable. The regulating member may comprise an inner core and an outer sheath disposed at least partially over the inner core. One of the inner core or outer sheath may be bioabsorbable while the other is elastic.

The apparatus may also comprise a second locking mechanism that is coupled with the constraining structure. The locking mechanism is adapted to releasably hold the constraining structure in a loop around the first and second anatomical structures. The locking mechanism may also be used to adjust length or tension in the constraining structure. The apparatus may also carry a therapeutic agent that may be released therefrom.

In another aspect of the present invention, a method for constraining a first and a second anatomical structure together comprises capturing the first and the second anatomical structures with a constraining structure that includes a motion limiting member. The motion limiting member provides a force resistant to relative movement of the first anatomical structure away from the second anatomical structure. The resistive force provided by the motion limiting member is regulated with a regulating member in engagement with the motion limiting member or constraining structure.

The motion limiting member may be at least partially encapsulated in a biodegradable material and thus the regulating step may comprise implanting the apparatus in a patient's body so as to at least partially erode away the biodegradable material from the motion limiting member thereby reducing stiffness of the motion limiting member. Upon erosion of the biodegradable material, the motion limiting member may also return to an unbiased contracted configuration which tightens the constraining structure. The method may also include the step of increasing erosion rate of the biodegradable material by providing an accelerating agent adapted to increase erosion of the biodegradable material in situ. The motion limiting member and/or the constraining structure may also comprise a damper element and the method further comprises damping relative motion between the first and the second anatomical structures. Sometimes the motion limiting member may be restrained with a restraining element such as a clip. The clip may increase stiffness of the motion limiting member. The constraining structure may comprise a tether structure and the method may comprise locking the tether structure in a loop around the first and second anatomical structures or adjusting tension in the constraining structure. Sometimes, the method may also include the step of releasing a therapeutic agent, such as a bone morphogenic protein. The method may also comprise locking the constraining structure so that its length or tension remains substantially fixed.

These and other embodiments are described in further detail in the following description related to the appended drawing figures.

DETAILED DESCRIPTION OF THE INVENTION

Figure 1A:
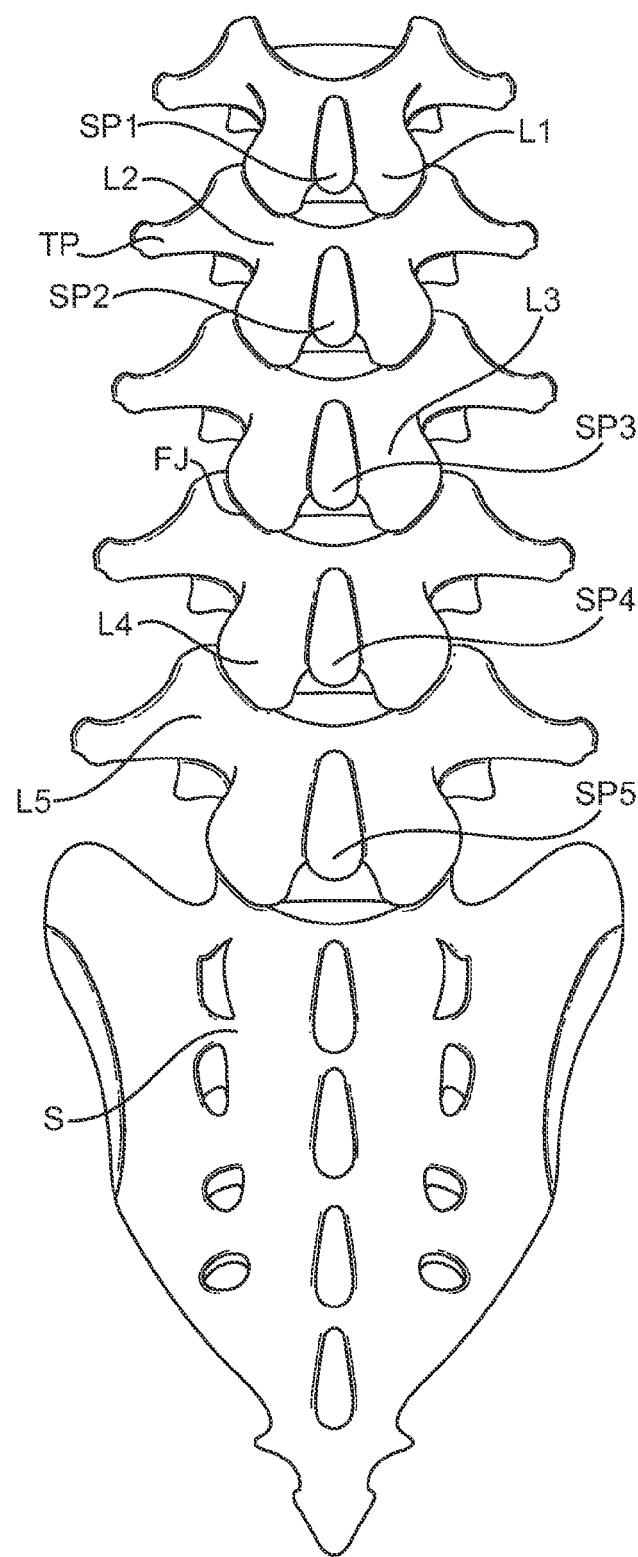
FIG. 1A is a schematic diagram illustrating the lumbar region of the spine.
Figure 1B:
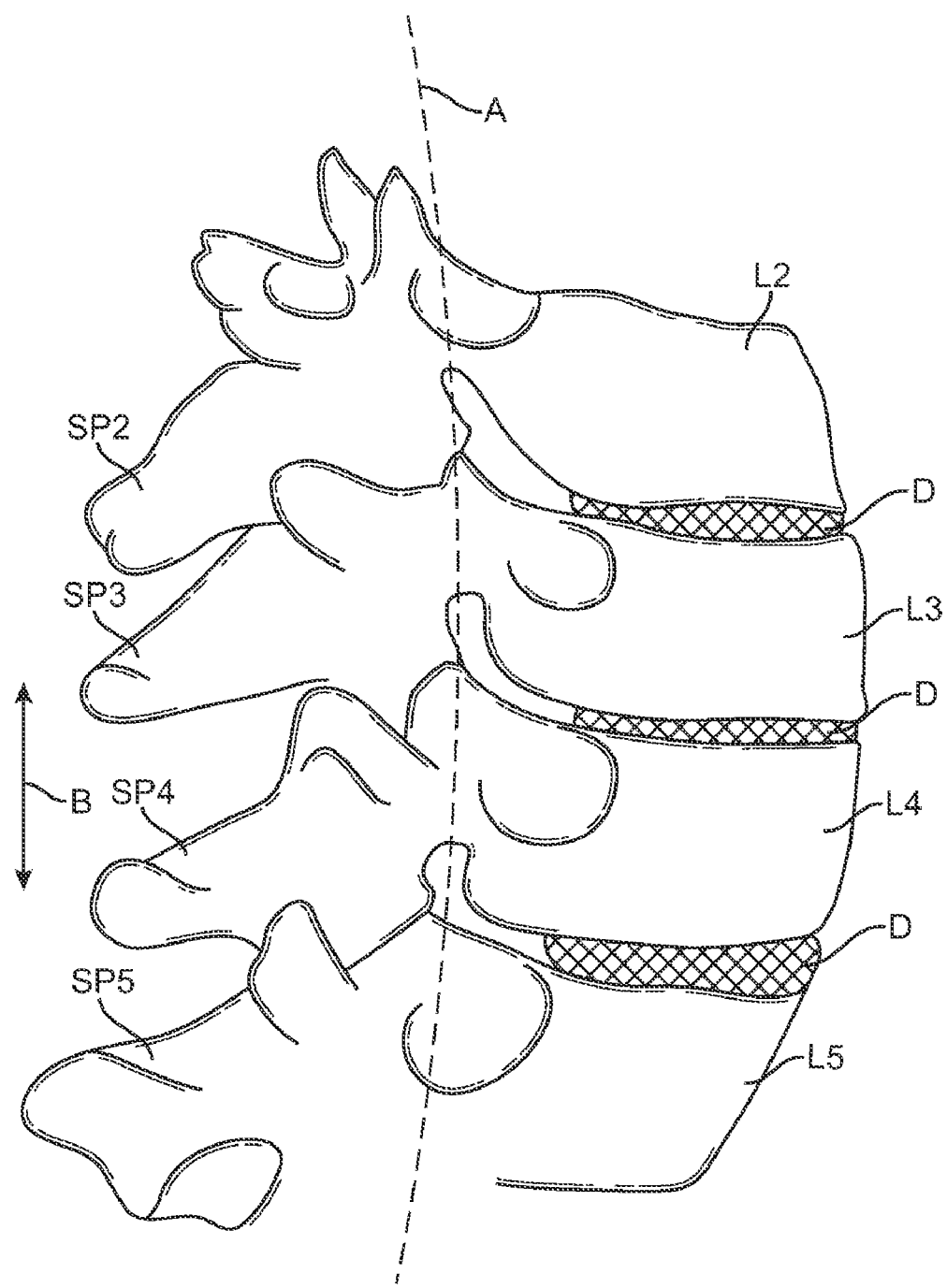
FIG. 1B a schematic illustration showing a portion of the lumbar region of the spine taken along a sagittal plane.

There are numerous internal surgical fixation procedures. Some of these are used for treating lower back pain. FIG. 1A is a schematic diagram illustrating the lumbar region of the spine including the spinous processes (SP), facet joints (FJ), lamina (L), transverse processes (TP), and sacrum (S). FIG. 1B is a schematic illustration showing a portion of the lumbar region of the spine taken along a sagittal plane and is useful for defining the terms "neutral position," "flexion," and "extension" that are often used in this disclosure.

As used herein, "neutral position" refers to the position in which the patient's spine rests in a relaxed standing position. The "neutral position" will vary from patient to patient. Usually, such a neutral position will be characterized by a slight curvature or lordosis of the lumbar spine where the spine has a slight anterior convexity and slight posterior concavity. In some cases, the presence of the constraint of the present disclosure may modify the neutral position, e.g. the device may apply an initial force which defines a "new" neutral position having some extension of the untreated spine. As such, the use of the term "neutral position" is to be taken in context of the presence or absence of the device. As used herein, "neutral position of the spinal segment" refers to the position of a spinal segment when the spine is in the neutral position.

Furthermore, as used herein, "flexion" refers to the motion between adjacent vertebrae in a spinal segment as the patient bends forward. Referring to FIG. 1B, as a patient bends forward from the neutral position of the spine, i.e. to the right relative to a curved axis A, the distance between individual vertebrae L on the anterior side decreases so that the anterior portion of the intervertebral disks D are compressed. In contrast, the individual spinous processes SP on the posterior side move apart in the direction indicated by arrow B. Flexion thus refers to the relative movement between adjacent vertebrae as the patient bends forward from the neutral position illustrated in FIG. 1B.

Additionally, as used herein, "extension" refers to the motion of the individual vertebrae L as the patient bends backward and the spine extends from the neutral position illustrated in FIG. 1B. As the patient bends backward, the anterior ends of the individual vertebrae will move apart. The individual spinous processes SP on adjacent vertebrae will move closer together in a direction opposite to that indicated by arrow B.

Figure 2:
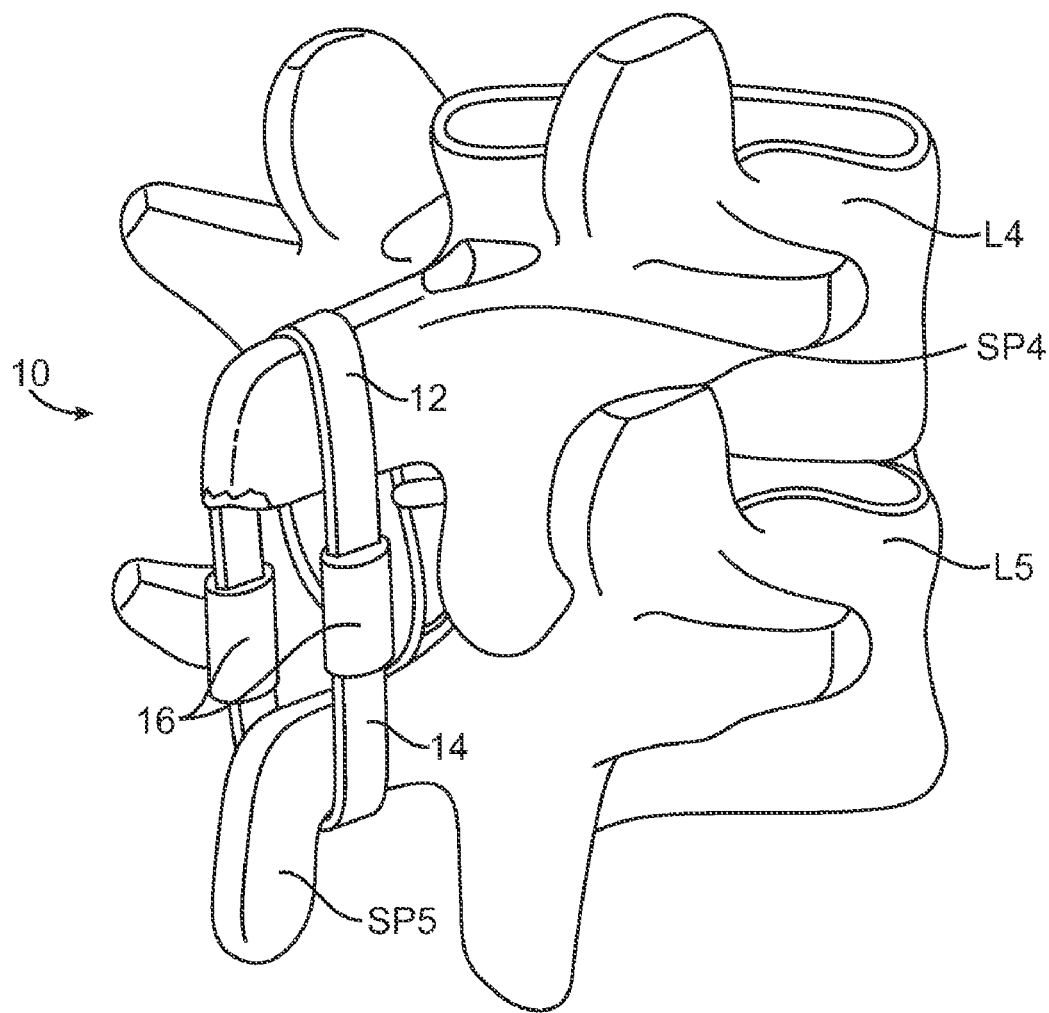
FIG. 2 illustrates a spinal implant of the type described in U.S. Pat. No. 7,458,981.

FIG. 2 shows a spinal implant of the type described in related U.S. Pat. No. 7,458,981, the entire contents of which are incorporated herein by reference. This implant is used as a treatment for back pain. It is coupled with one or more pairs of spinous processes, or a spinous process and the sacrum, and provides an elastic restraint to the spreading apart of the spinous processes during flexion. As illustrated in FIG. 2, an implant 10 typically comprises a tether structure having an upper strap component 12 and a lower strap component 14 joined by a pair of compliance elements 16. The upper strap 12 is shown disposed over the top of the spinous process SP4 of L4 while the lower strap 14 is shown extending over the bottom of the spinous process SP5 of L5. The compliance element 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinous processes which provides a force that resists flexion. The force increases as the processes move further apart. Usually, the straps themselves will be essentially non-compliant so that the degree of elasticity or compliance may be controlled and provided solely by the compliance elements 16.

The constraint device illustrated in FIG. 2 is promising, yet the device typically provides only relatively constant fixation properties such as stiffness, size, and tightness, until the device is removed. Thus, the constraint device provides a continuous stress shield to the tissue it supports. This may be desired during the early phases of healing, but may not be desirable in the later phases of healing because the stress shielding may hamper tissue repair as the tissue remodels to accommodate a lower load. Additionally, over long periods of time, excessively high fixing forces can cause tissue necrosis. In other cases, it may also be desirable to permit a small amount of micromotion or a small amount of loading as this can facilitate tissue repair. Therefore, there is a need to provide a constraint device such as that illustrated in FIG. 2, but which also can vary the properties of the device, such as the constraining force or tension exerted, as well as the stiffness and damping, during the healing or tissue regeneration process. In particular, such a device is preferably adjustable by a physician during the healing process or the device may automatically vary its constraining properties over time.

Figure 3A:
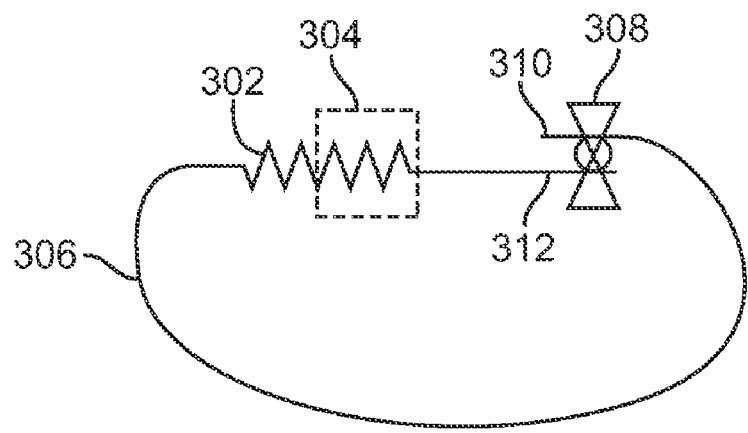
FIGS. 3A-3C illustrate an exemplary embodiment of a bioabsorbable regulating member in a constraint device.
Figure 3B:
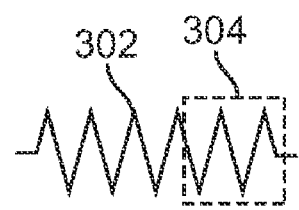
Figure 3C:
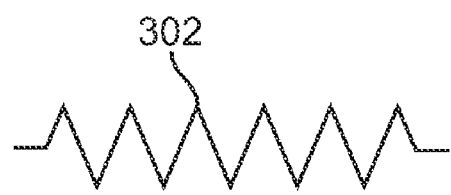

FIGS. 3A-3C illustrate one exemplary embodiment of a regulating member that may be used with a constraint device in order to vary the constraining forces over time. In FIG. 3A, a tether 306 is coupled with a motion limiting member, here a compliance member 302 and a tension/sizing adjustment mechanism 308 for locking the device length into a desired position. In this exemplar embodiment a portion of compliance member 302 is encapsulated in a bioabsorbable material 304 such as polylactic acid (PLA) which transfers load to the encapsulating layer, increasing stiffness of the system. In other embodiments, the entire compliance member may be encapsulated. Other bioabsorbable materials are known in the art and include but are not limited to materials such as polyglycolic acid (PGA). The PLA or PGA may be either the levo or dextro isomers or racemic mixtures may be used. Compliance member 302 is a coil spring although it may also be an elastomeric element or other spring-like elements may be used. The tether structure 306 encircles two anatomical structures and the loop size is adjusted using locking mechanism 308 in order to keep the two anatomical structures from moving away from one another during the healing process. As the two anatomical structures move relative to one another, spring 302 extends and therefore exerts a compressive force against the two anatomical structures which restrains their movement and keeps them apposed against one another. Tether structure 306 may be a wire, suture, cord, cable, ribbon or similar structures to form a loop that encircles two anatomical structures. Tether 306 may be a textile, a metal or a polymer such as ultra high molecular weight polyethylene (UHMWPE) or polyethylene terapthalate (PET). Other embodiments of tether structures and compliance members are disclosed in U.S. Patent Publication No. 2008/0319487; the entire contents of which are incorporated herein by reference. Locking mechanism 308 allows ends 310, 312 of tether 306 to be joined and fixed together so as to adjust the size of the loop and its initial tension. Exemplary locking mechanisms 308 are disclosed in copending U.S. patent application Ser. No. 12/479,016 and U.S. Provisional Patent Application No. 61/059,543, both incorporated herein by reference. Other locking mechanisms such as crimps, clamps, cleats, knots, etc. may also be used to hold the tether structure in a desired loop size. Bioabsorbable material 304 encapsulates all or a portion of the compliance member 302 and prevents the encapsulated portion of spring 302 from expanding and contracting, thereby effectively stiffening the spring 302. Thus, the tether structure will exert a greater force resistant to motion of two anatomical structures away from one another.

After the tether structure 306 is implanted into a patient, the bioabsorbable material 304 will begin to erode away from the spring 302. After a period of time, enough of the material 304 erodes away and the load is transferred to the spring 302 which becomes more compliant. Thus, spring 302 regains its normal unencapsulated spring properties, in this case, becoming a less stiff spring and providing less restraint force than while encapsulated. FIG. 3B illustrates the spring 302 encapsulated by bioabsorbable material 304 and FIG. 3C shows the spring 302 after the bioabsorbable material has eroded away from the spring 302. Thus, in this embodiment, the bioabsorbable material 304 regulates the force provided by compliance member 302 over time.

Figure 10:
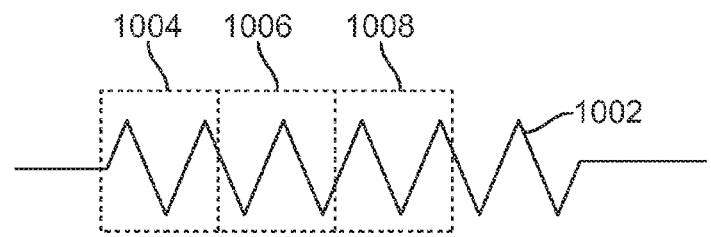
FIG. 10 illustrates a compliance member having a plurality of regulating members.

In some embodiments, a plurality of regulating members may be disposed on the compliance member in order to further vary the compliance member properties over time. For example, in FIG. 10, a compliance member 1002, here a coil spring, has three bioabsorbable blocks 1004, 1006 and 1008 disposed around different portions of the compliance member 1002. Each of the bioabsorbable blocks has a different bioabsorption rate, therefore, for example, block 1004 will be absorbed first decreasing stiffness of compliance member 1002 slightly, followed by absorption of block 1006 further decreasing stiffness and eventually followed by absorption of block 1008, returning the compliance member 1002 to its natural state and stiffness. Bioabsorption of the various blocks may be timed with various stages in the healing process or the rate of bone formation, as well as additional treatments applied by the physician, such as agents that affect absorption rates or ultrasound.

Figure 4:
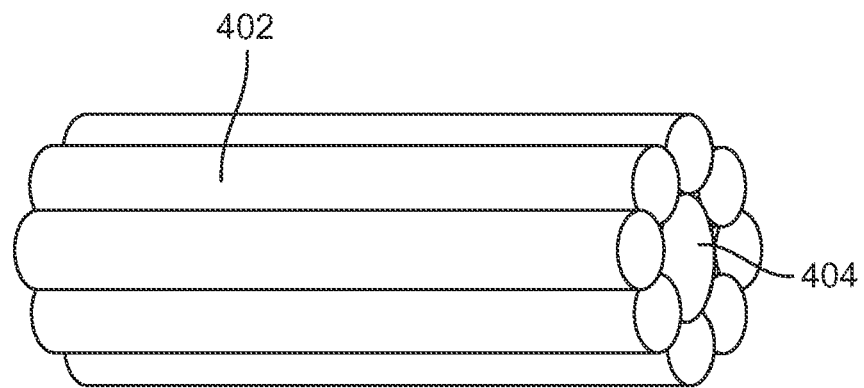
FIG. 4 illustrates an alternative embodiment of a bioabsorbable regulating member.

FIG. 4 illustrates an alternative embodiment of a compliance and regulating member that also uses a bioabsorbable material. In FIG. 4, a plurality of outer fibers 402 are disposed around a central core 404. The outer fibers 402 are elastic and serve as the compliance member instead of a spring and the core 404 is fabricated from an inelastic bioabsorbable material such as PLA or PGA or any of the isomers previously disclosed. The inner core 404 prevents the elastic fibers from expanding and therefore results in a stiffer compliance member. As the inner core is bioabsorbed, the elastic fibers take up the load and provide the compressive force which resists movement of the constrained anatomical structures. The elastic fibers may be manufactured from an elastic material such as silicone, polyurethane elastomer or other elastic materials. Additionally, in other embodiments, the outer fibers may be the inelastic bioabsorbable portion of the regulating member and the inner core may be the elastic portion of the compliance member. Additional inelastic, non-bioabsorbable fibers may provide a secondary, permanent limit to elongation of the elastic portion.

In the embodiment of FIGS. 3A-3C, the compliance member is a discrete component, separate from the tether structure. In other embodiments, the tether structure and compliance member may be integral with one another. For example, the tether may be fabricated from an elastic strap similar to a bungee cord. Thus, as the tether stretches, the elastic fibers in the elastic strap are stretched and they provide the compressive force that resists movement of the anatomical structures away from one another.

Figure 5A:
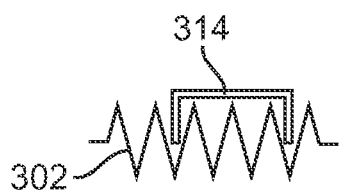
FIGS. 5A-5B illustrate several embodiments of a mechanical clip used as a regulating member.
Figure 5B:
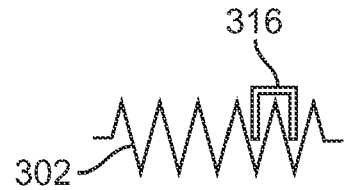

In alternative embodiments, clips or other restraints may be used to regulate the compliance member, such as in FIGS. 5A-5B. In FIG. 5A, a clip 314 is applied to a section of coil spring 302, thereby effectively immobilizing a portion of the spring 302 resulting in a stiffer spring 302. In FIG. 5B, a shorter section of spring 302 is immobilized by a smaller clip 316. This still results in a stiffer spring, but not as stiff as in FIG. 5A where a longer section of spring 302 is immobilized. To decrease spring 302 stiffness, clip 314 or 316 may be removed by a physician in another surgical procedure as the healing process continues, or the clips 314, 316 may be fabricated from a bioabsorbable material such as PLA or PGA in a manner similar to that previously described with respect to FIGS. 3A-3C. This benefits patients with conditions where stiffer or more rigid fixation is required early in the healing processes and more compliant fixation is sufficient or even beneficial after a period of healing. The advantage of using a bioabsorbable material is that the process does not require additional surgical procedures. In addition to using a single clip, multiple clips may be used to clip several section of the spring 302. Furthermore, clips with different bioabsorption rates may be used so that some clips are absorbed before others, thereby further regulating or modulating the forces provided by spring 302.

Figure 6:
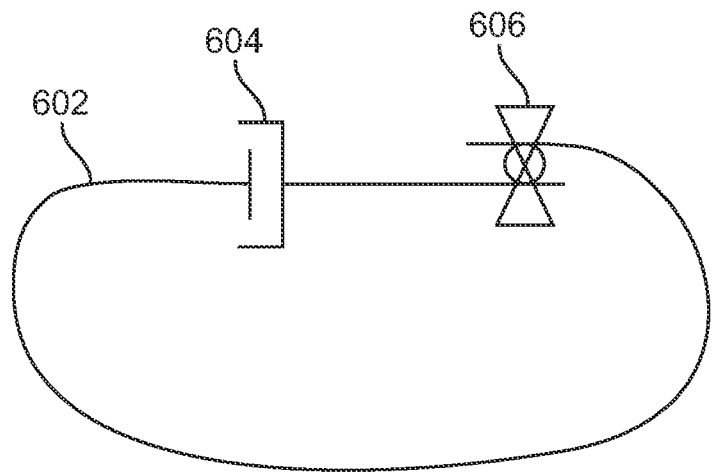
FIG. 6 illustrates the use of a damper as the regulating member.

The regulating member may also comprise a damper element which reduces transient loads or motions in the tether structure. Additionally, an optional damper element may be included with the compliance member. FIG. 6 illustrates an exemplary embodiment of a tether structure 602 in series with a damper 604 and having a tensioning or sizing adjustment mechanism 606 such as the mechanism 308 described above in FIGS. 3A-3C. In this embodiment, damper 604 may be a dashpot or shock absorber which typically resists motion due to viscous properties. Thus, transient loads or motions will be reduced by the damper 604. The damper may be adjusted to increase or decrease its damping ability. For example, a physician may adjust a clamping force or orifice size in the damper with fasteners such as screws or bolts or a bioabsorbable material such as those previously described may be used to reduce friction between moving components or that restrict fluid flow.

In various constraint devices, dampers and compliance elements may be combined in different configurations to achieve desired device performance characteristics. For example, in FIG. 7A, a tether structure 710 is coupled with both a damper 708 and a compliance element 704. The compliance element has an optional regulating member 706 such as the bioabsorbable cover previously described or clip also previously described. The compliance member 704 is in parallel with the damper 708. The ends of the tether structure 712, 714 are secured together with a tension and sizing adjustment mechanism 702.

Figure 7A:
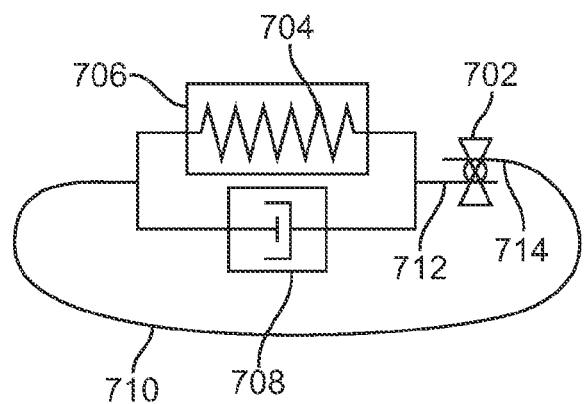
FIGS. 7A-7C illustrate various configurations of compliance members and dampers in a constraining device.
Figure 7B:
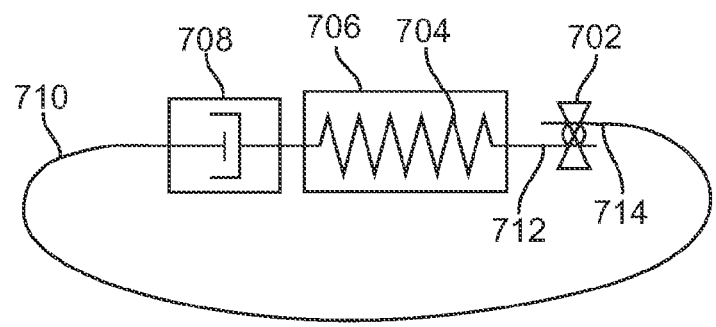
Figure 7C:
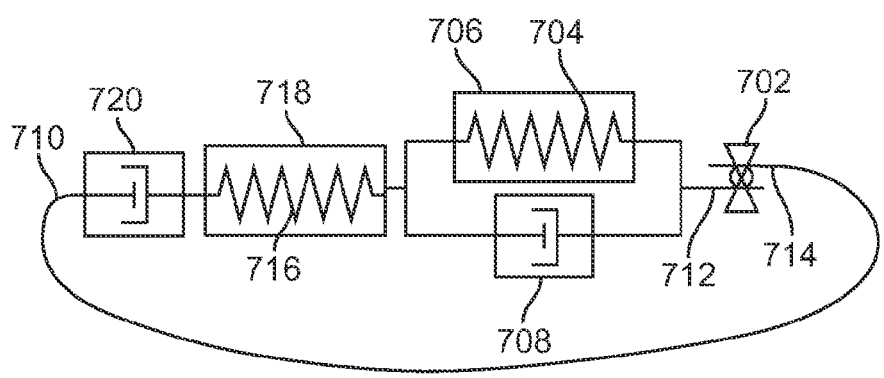

FIG. 7B is similar to the embodiment of FIG. 7A with the exception that this time the damper 708 is in series with the compliance member 704. FIG. 7C illustrates yet another embodiment with multiple dampers and multiple compliance members. In this exemplary embodiment, compliance member 704 is in parallel with damper 708 and compliance member 716 is in series with damper 720. Compliance members 704, 716 optionally have a regulating member 706, 718 comprising a bioabsorbable cover or a clip such as those previously described above. Alternative embodiments of compliance devices may have two sets of compliance members, preferably symmetrically disposed with one on each side of the spinal segment midline. Additionally, any combination of damper and/or regulating member may also be included in the constraint device. For example, a constraint device may include two compliance members, two dampers, and two regulating members, with one of each on opposite sides of the spinal segment midline. One of skill in the art will appreciate that many configurations are possible.

Figure 8A:
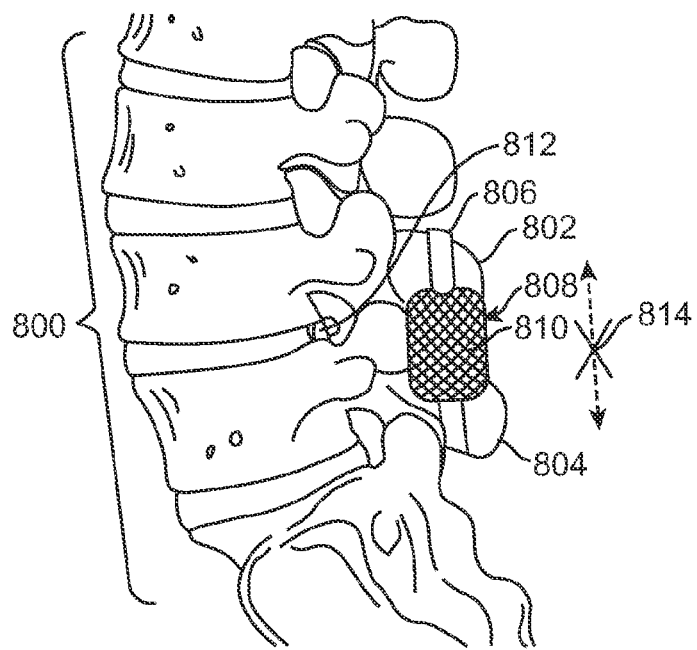
FIGS. 8A-8B illustrate the use of a constraint device having a regulating member in the treatment of a spinal segment.
Figure 8B:
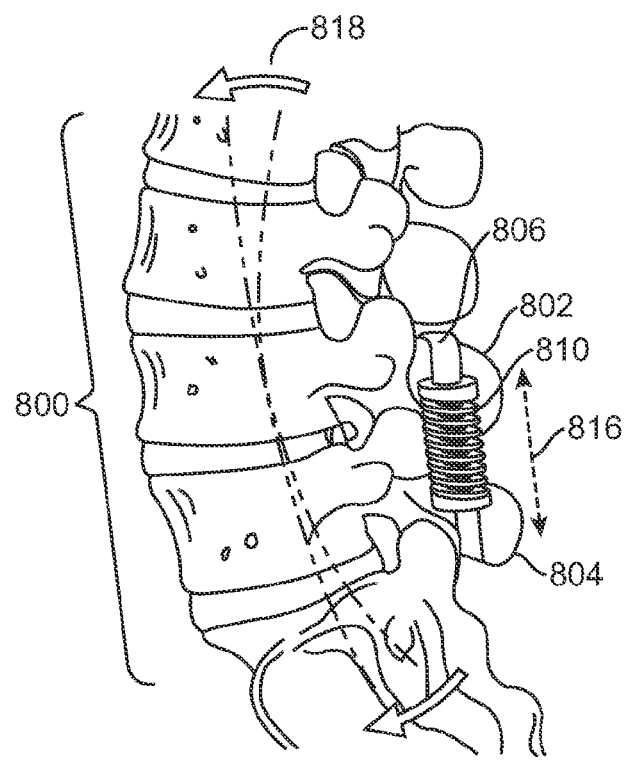

FIGS. 8A-8B illustrate an exemplary use of the constraining devices described above. In FIG. 8A, a herniated disc 812 bulges out from in between vertebral bodies in a spinal segment 800. Sometimes a herniated disc fragment may be removed in a procedure commonly called microdiscectomy. In order to facilitate healing of the herniation (with or without microdiscectomy), a constraining device is implanted around the adjacent spinous processes. The minimally invasive implantation procedure is disclosed in greater detail in U.S. Patent Publication Nos. 2008/0108993; and 2008/0262549; the entire contents of which are incorporated herein by reference. Here, an inelastic tether structure 806 is wrapped around an upper spinous process 802 and a lower spinous process 804, or to a sacrum (not illustrated). The tether structure 806 includes a compliance member 810 that has been encapsulated in a rigid bioabsorbable material 808 such as PLA or PGA or isomers thereof. A second encapsulated compliance member may also be included in the constraining device, opposite the first (not shown) on the other side of the spinal midline. The rigid bioabsorbable material limits the compliance member 810 from expanding and contracting, therefore flexion of spinal segment 800 is restricted in the direction of arrow 814. As the herniation heals, the bioabsorbable material 808 is absorbed exposing compliance member 810 and allowing it to expand and contract more freely according to its spring properties. This restores normal motion of spinal segment 800 in the direction of arrow 818 and arrow 816 while still providing some stabilization and thus helping to prevent recurrence of the injury. FIG. 8B illustrates the compliance member after the bioabsorbable material 808 has been absorbed and the spinal segment 800 is slightly in flexion.

Figure 9A:
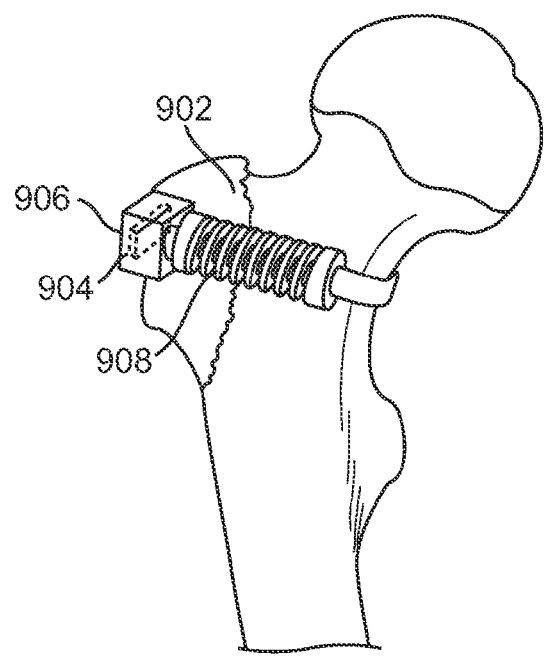
FIG. 9A-9B illustrate the use of a constraint device having a regulating member in the treatment of a fractured bone.
Figure 9B:
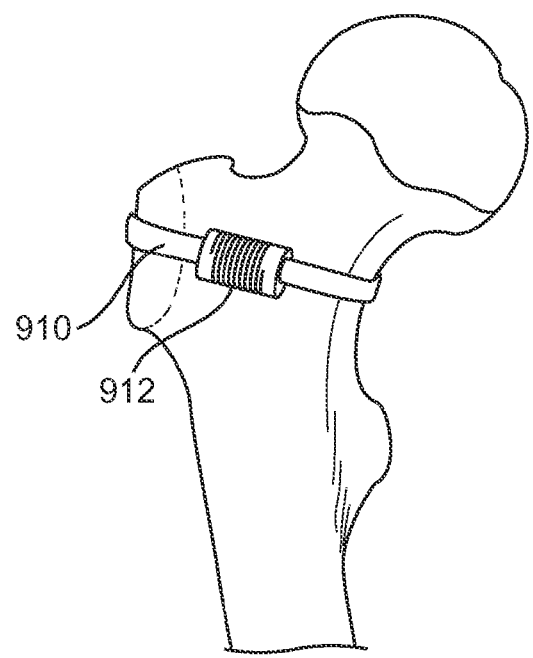

FIGS. 9A-9B illustrate another exemplary use of the constraining devices described above. Patients with a fracture of the greater trochanter 902 can benefit from a constraining device that applies more compression to the fracture during the initial phases of healing, and then less compression across the fracture when the bones are substantially healed. In FIG. 9A, a length of tether 904 is embedded in a bioabsorbable block of material 906 such as PLA or PGA, thereby effectively shortening the overall length of the tether 904. This causes an elongation to the compliance element 908, causing a compressive force across the fracture site 902. After healing, as seen in FIG. 9B, bioabsorption of the block 906 frees the previously embedded portion of the tether 910 which increases the total length of the tether allowing compliance member 912 to relax. This reduces the compression force on the healed bone. In other embodiments, the compliance element 908 may be encapsulated in the bioabsorable block of material similar to the embodiment of FIGS. 8A-8B.

Figures 11A, 11B:
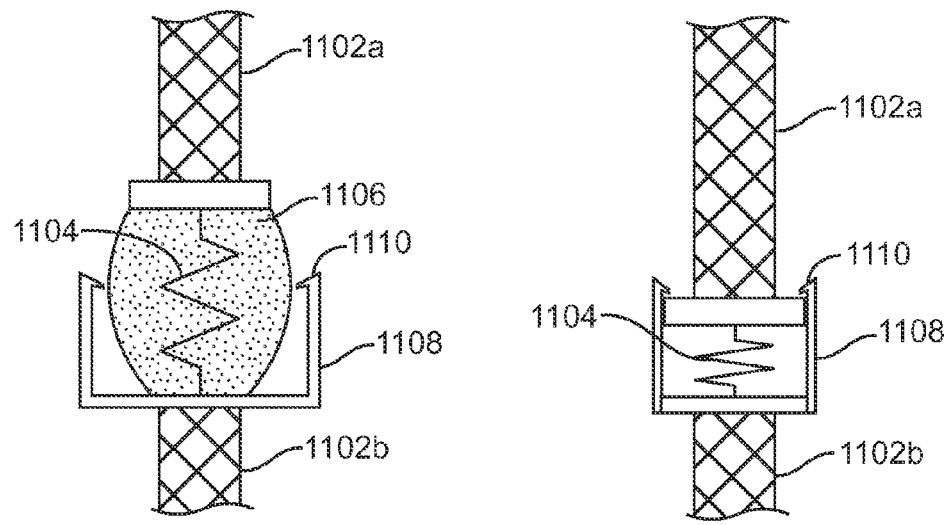
FIGS. 11A-11B illustrate an exemplary embodiment of a bioabsorbable regulating member.

The previously disclosed embodiments all apply an initially higher constraint force to the anatomical structures being fixed together and then the force is reduced over time. It is also possible to provide constraint devices where the initial force is lower and then increases over time. For example, FIGS. 11A-11B illustrate an exemplary embodiment of a modulated constraint device where the device tightens over time. An upper tether 1102a and a lower tether 1102b are joined together with a compliance member 1104 such as a spring or elastomeric member. The compliance member 1104 is embedded in a bioabsorbable material 1106 such as PLA or PGA while the compliance member 1104 is deformed into an expanded configuration. The device also includes an optional locking mechanism 1108 having a pair of locking arms 1110. In use, the device is implanted while the compliance member 1104 is in the expanded configuration. Over time, the bioabsorbable material 1106 will erode away and thus compliance member 1104 will return to its undeformed configuration, thereby drawing the upper and lower tether portions 1102a, 1102b together, tightening the device and/or increasing the tension in the device. The optional locking mechanism 1108 will lock the compliance member into the collapsed configuration, here by engaging the locking arms 1110 with a distal region of the upper tether 1102a thereby maintaining the device in a tighter configuration around the target tissue being repaired. The locking mechanism may comprise a snap fit, detent mechanism, press fit, or other mechanism known to those skilled in the art. This embodiment is advantageous in that it allows tightening of the device as healing occurs and allows slack to be taken up without requiring a postoperative procedure. Compliance of the compliance member may be tailored to provide desired properties. For example, a very stiff spring provides little compliance once the resorbable layer has eroded away and may generate or release relatively significant force in the device as it relaxes. Additionally, this configuration of modulated constraining device may also be used in series or parallel with any of the other features described herein. In still other embodiments, a bioabsorable clip or wedge member (not illustrated) may be used to hold the compliance member in an expanded configuration. The clip or wedge may be removed by a surgeon or allowed to bioabsorb away, permitting the compliance member to return to its unbiased configuration. It can be appreciated by one skilled in the art that similar mechanisms are feasible, including where the compliance member is embedded in the resorbable component in a compressed configuration, such that when the resorbable component erodes and the compliance member is released the constraint loosens.

Figure 12:
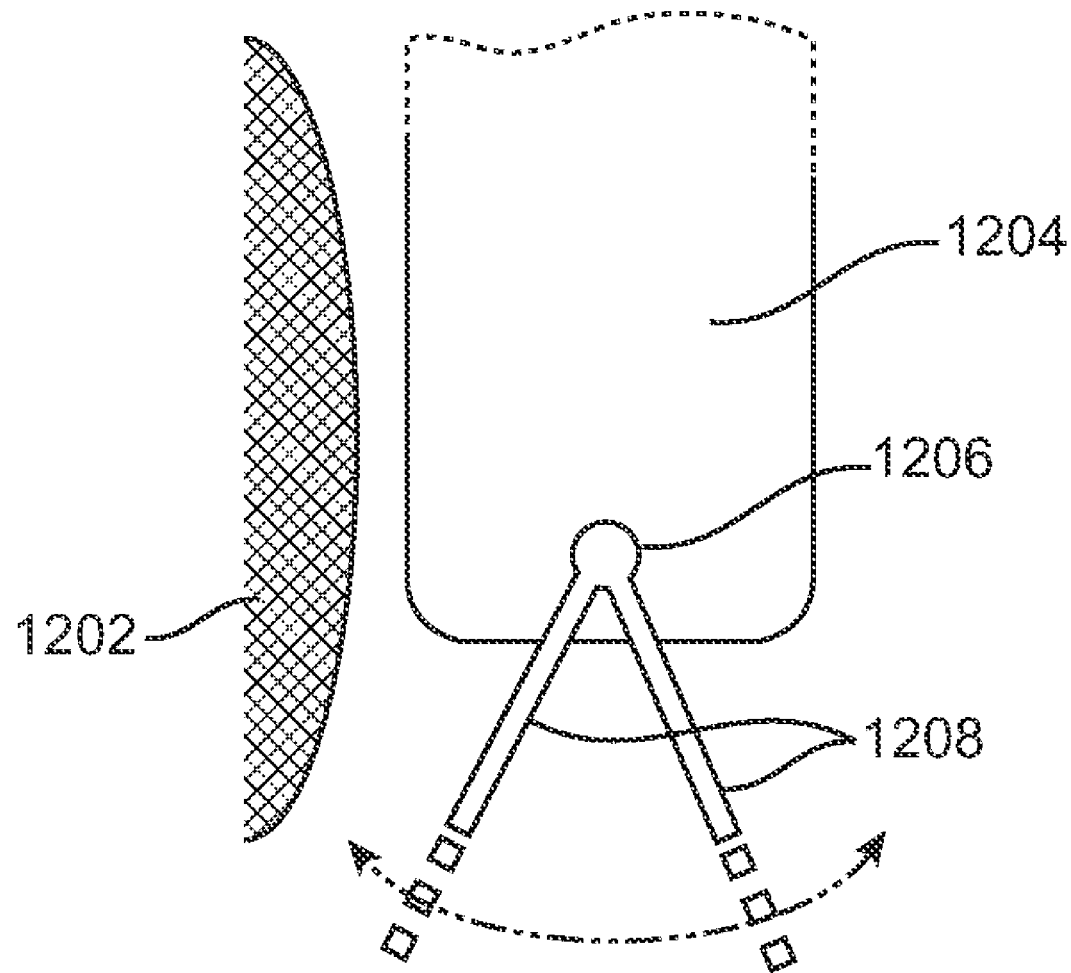
FIG. 12 illustrates a regulating member having a pin joint.

FIG. 12 illustrates an exemplary embodiment of a constraining device having a regulating member formed from a pin joint. The constraining device includes a compliance member 1204 that is pivotably coupled a tether 1208 with a pin 1206 such that the tether 1208 can pivot relative to the compliance member 1204. As tissue 1202 adjacent the device expands and contracts, loading on the constraining device may change. Therefore, this mechanical approach allows the compliance member 1204 to pivot relative to the tether 1208 which re-aligns the constraining device, thereby regulating loads transferred to the compliance member 1204 in response to the adaptation of surrounding tissue 1202.

Furthermore, any of the embodiments discussed above may also include various therapeutic agents or drugs such as bone morphogenic proteins that may be used to induce the formation of bone, cartilage, or other skeletal tissues. The therapeutic agents may be included in the bioabsorbable materials so that as the bioabsorbable material is absorbed, it releases the therapeutic agent.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for constraining first and second anatomical structures together, said method comprising:
   capturing the first and the second anatomical structures with an apparatus having a constraining structure, the constraining structure having a motion limiting member which provides a force resistant to relative movement of the first anatomical structure away from the second anatomical structure; and
   regulating the resistive force provided by the motion limiting member with a regulating member in engagement with the motion limiting member or the constraining structure,
   wherein the motion limiting member is at least partially encapsulated in a biodegradable material and wherein the regulating comprises implanting the apparatus in a patient's body so as to at least partially erode away the biodegradable material from the motion limiting member thereby allowing the motion limiting member to return to an unbiased contracted configuration which tightens the constraining structure.

2. The method of claim 1, wherein the first anatomical structure comprises a first spinous process and the second anatomical structure comprises a second spinous process or sacrum.

3. The method of claim 2, wherein a third spinous process is disposed between the first spinous process and the second spinous process or sacrum.

4. The method of claim 1, wherein the first anatomical structure comprises a bone and the second anatomical structure comprises a portion of the bone fractured or cut therefrom.

5. The method of claim 4, wherein the bone comprises a greater trochanter.

6. The method of claim 1, wherein the regulating member comprises a pin-joint pivotably coupling a compliance member and the constraining structure so as to allow realignment of the constraining apparatus in response to expansion or contraction of adjacent tissue.

7. The method of claim 1, further comprising locking the constraining structure so that length or tension therein remains substantially fixed.

8. The method of claim 1, further comprising increasing an erosion rate of the biodegradable material.

9. The method of claim 8, wherein the step of increasing erosion comprises providing an accelerating agent adapted to increase erosion of the biodegradable material in situ.

10. The method of claim 1, wherein the constraining structure comprises a damper element and the method further comprises damping relative motion between the first and the second anatomical structures.

11. The method of claim 1, wherein the motion limiting member comprises a damper element.

12. The method of claim 1, wherein the regulating comprises restraining the motion limiting member with a restraining element.

13. The method of claim 12, wherein the restraining comprises providing a clip engaged with the motion limiting member so as to increase stiffness thereof.

14. The method of claim 1, wherein the constraining structure comprises a tether structure and the method further comprises locking the tether structure in a loop around the first and second anatomical structures.

15. The method of claim 1, further comprising adjusting tension or size in the constraining structure.

16. The method of claim 1, further comprising a step of releasing a therapeutic agent.

17. The method of claim 16, wherein the therapeutic agent comprises a bone morphogenic protein.

* * * * *